United States Patent [19]

Cure

[11] 4,342,633
[45] Aug. 3, 1982

[54] OXYGEN SENSOR
[75] Inventor: Omer Cure, Diepenbeek, Belgium
[73] Assignee: Electro-Nite Co., Philadelphia, Pa.
[21] Appl. No.: 26,142
[22] Filed: Apr. 2, 1979
[30] Foreign Application Priority Data Apr. 6, 1978 [FR] France .................................. 78 10229

[51] Int. Cl.³ ............................................ G01N 27/58
[52] U.S. Cl. ................................................. 204/195 S
[58] Field of Search ............... 204/1 S, 195 S; 422/98

[56] References Cited

U.S. PATENT DOCUMENTS

| | | | |
|---|---|---|---|
| 3,378,478 | 4/1968 | Kolodney et al. | 204/195 S |
| 3,619,381 | 11/1971 | Fitterer | 204/195 S |
| 3,630,874 | 12/1971 | Olette et al. | 204/195 S |
| 3,657,094 | 4/1972 | Hans et al. | 204/195 S |
| 3,668,099 | 6/1972 | Rittiger et al. | 204/195 S |
| 3,723,279 | 3/1973 | Fruehan et al. | 204/195 S |
| 3,752,753 | 8/1973 | Fitterer | 204/195 S |
| 3,758,397 | 9/1973 | Rittiger et al. | 204/195 S |
| 3,784,459 | 1/1974 | Jackson | 204/194 S |
| 4,105,507 | 8/1978 | Von Krusenstierna et al. | 204/195 S |
| 4,141,813 | 2/1979 | Kita et al. | 204/195 S |

FOREIGN PATENT DOCUMENTS

| | | | |
|---|---|---|---|
| 7509314 | 4/1978 | France. | |
| 1081545 | 8/1967 | United Kingdom | 204/195 S |

OTHER PUBLICATIONS

E. T. Turkdogan et al., The General Meeting of Am. Iron & Steel Inst., pp. 1 and 8-11, May 23, 1968.

Primary Examiner—G. L. Kaplan
Attorney, Agent, or Firm—Seidel, Gonda, Goldhammer & Panitch

[57] ABSTRACT

The device for measuring active oxygen content in a bath of molten metal includes an electrochemical cell having a consummable shield for protecting the cell from thermal shock during immersion.

8 Claims, 2 Drawing Figures

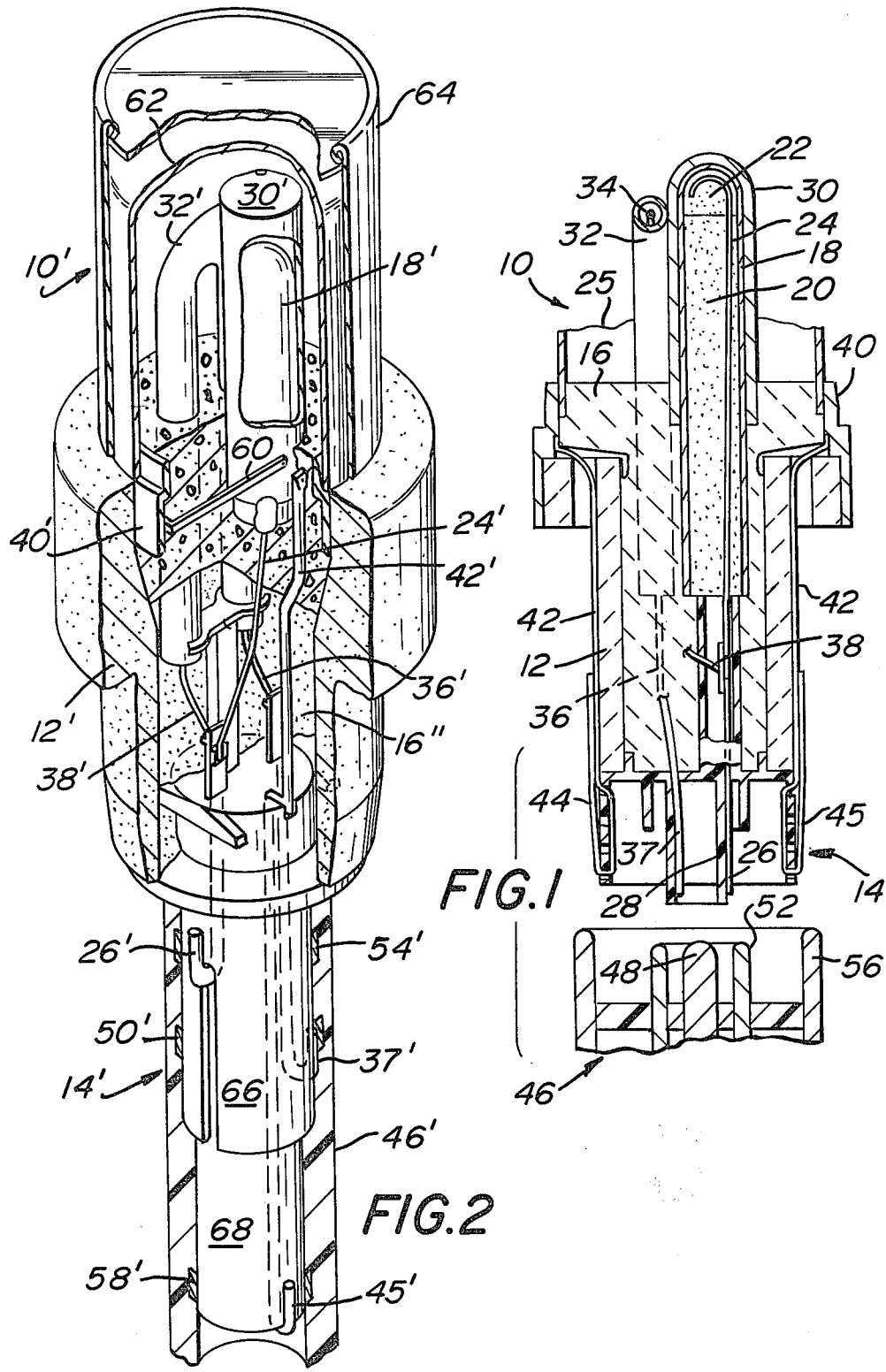

OXYGEN SENSOR

BACKGROUND

It is known to use an electrochemical cell for measuring the difference in oxygen potential between a bath of molten metal, such as iron or steel, and a reference. Such known devices are mounted on the end of a carrier such as a tube or rod.

In the course of numerous practical experiments with such known devices, I have found that the measurements were often uncertain. It was not possible to obtain measurements with sufficient reliability. As a result of further research, I have found that upon entrance of the measuring head into the bath of molten metal the character of uncertainty was due to failure resulting in thermal shock. The purpose of the present invention is to solve this difficulty in a practical manner without substantially increasing the cost or complicating the fabrication of the device.

U.S. Pat. Nos. 3,619,381 and 3,752,753 disclose oxygen sensors of different construction and recognize the problem of thermal shock. Applicant's solution of this problem differs materially from the solution disclosed in said patents.

SUMMARY OF THE INVENTION

The present invention is directed to an oxygen sensor for measuring the active oxygen content of baths of molten metal. The device comprises a measuring head which is adapted to fit on the end of a carrier. The head has a portion which supports an electrochemical cell. The cell includes a reference material and an oxygen ion conductor. A shield protects the conductor and cell from thermal shock during immersion and cooperates with the head to envelop said conductor. The shield has an inner periphery juxtaposed to the outer periphery of said conductor. The shield is constructed so as to be consummable by a bath of molten metal within 0.1 to 10 seconds for exposing said conductor to the bath of molten metal.

It is an object of the present invention to provide a novel oxygen sensor which assures greater accuracy and reproducability for measuring active oxygen levels up to 1000 ppm.

For the purpose of illustrating the invention, there is shown in the drawings a form which is presently preferred; it being understood, however, that this invention is not limited to the precise arrangements and instrumentalities shown.

FIG. 1 is a sectional view of an oxygen sensor in accordance with the present invention.

FIG. 2 is a sectional view of another embodiment of the present invention.

Referring to the drawings in detail, wherein like numerals indicate like elements, there is shown in FIG. 1 an oxygen sensor designated generally at 10. Sensor 10 includes a heat 12 intended to be fitted within one end of a hollow carrier such as a paperboard tube not shown. The carrier may be made from other materials such as wood. The head 12 is made from a refractory or ceramic material so as to be non-reactive material with the bath of molten metal. The head as shown in cylindrical with one end being closed by a contact member 14 preferably made from a material such as polymeric plastic. The head is filled with a refractory cement 16.

The head as thusly described is similar to that disclosed in French Pat. No. 7509314.

The electrochemical cell includes an oxygen ion conductor 18 preferably made in the form of a tube closed at one end and from a material such as stabilized zirconium oxide. The open end of the conductor 18 is embedded in the cement 16. Within the conductor 18, there is provided a reference electrode 22. The reference electrode 22 is preferably $CrCr_2O_3$. The remainder of the conductor 18 is filled with an inert filler such as $Al_2O_3$. An electrical conductor 24, preferably of molybdenum has one end embedded in reference electrode 22. The other end of conductor 24 is connected to a compensating lead having a contact portion 26 supported by the outer periphery of a cylindrical projection 28 on the contact member 14.

A shield 30 cooperates with the head 12 to envelop the conductor 18. The inner diameter of shield 30 has a close sliding fit with the out diameter of conductor 18 so as to be juxtaposed thereto. The shield 30 is preferably a metal shield so as to be consummable by the bath within 0.1 to 10 seconds. A consummable thin walled cap 25 protects the cell from slag during immersion.

The wall thickness of shield 30 is chosen mainly as a function of the temperature ranges of the baths of molten metal and the characteristics of the electrochemical cell being used. The shield 30 considerably dampens the thermal shock produced during immersion of the sensor 10 in the bath of molten metal thereby reducing the risks of failures. It has been determined that this effect is obtained when shield 30 effectively protects the housing 18 from direct thermal contact with the metal of the bath during a time of approximately 0.3 to approximately 5 seconds after the initial immersion. Satisfactory results have been attained by using 0.008 to 0.010 inch thick walls for the shield 30 made from low carbon steel. it is important that the conductor 18 of zirconium oxide be in direct contact with the bath subsequent to the shield 30 being consumed in order to obtain a precise measurement within an acceptable time.

If desired, the head 12 may include a U-shaped tube 32 of quartz or the like supported by a post connected to contact member 14. Tube 32 contains a thermocouple having a hot junction 34. The thermocouple wires are designated 36, 38. Wire 36 is connected to a compensating lead having a contact portion 37 exposed on the inner periphery of projection 28. Wire 38 is connected to conductor 24. Accordingly, the thermocouple may be connected to recording equipment by way of contact portions 26, 37.

In order to permit the measurement of the difference in active oxygen potential between the bath of molten metal and the reference electrode 22, the head 12 may be surrounded by a metal electrode 40 which is the positive contact of the cell. One end of one or more conductors 42 is connected to electrode 40. The other end of conductor 42 is a contact portion 45 supported by a cylindrical projection 44 on the contact member 14.

A connector 46 is provided within the carrier for coupling the sensor 10 to a two-pen recorder. Connector 46 includes a post 48 for engagement with contact portion 37 and a ring contact 52 for contact with contact portion 26. The connector 46 also includes a ring contact 56 for contact with the contact portion 45. Elements 48, 52 and 56 are insulated from one another and electrically coupled to the recorder.

In FIG. 2, there is illustrated another embodiment of the present invention wherein the oxygen sensor is designated 10'. The sensor 10' is identical with the sensor 10 except as will be made clear hereinafter. Hence, corresponding elements are identified by corresponding primed numerals.

In FIG. 2, the thermocouple tube 32' and the shield 30' are provided with protection in the form of fusable metal cap 62 and a paper shield 64. A conductor 60 extends between the metal electrode 40' and a portion of the shield 30' embedded within the cement 16'. Between the cement 16' and the contact member 14', there may be provided epoxy dielectric material 16''.

The contact member 14' includes plastic tubes 66, 68. The tube 66 is provided with different length slots. Contact portion 26' extends through one slot in tube 66 and contact portion 37' extends through the other slot in tube 66. Tube 68 is fixed to tube 66. Tube 68 is notched at its lower end for receiving the contact portion 45'. Thus, the contact portions 26', 37' and 45' are at different elevations for mating contact with their respective ring contacts 54', 50' and 58' on the connector 46'.

Since the sensors operate in the same manner, only sensor 10' will be described. The cap 62 and shield 64 are consumed as the sensor is immersed into the bath of molten metal. Thereafter, shield 30' melts down to the exposed surface of cement 16'. The ring portion of shield 30' below the exposed surface of cement 16' remains as part of the cell. Conductor 18' is now exposed to the bath. The cell generates an emf which is proportional to the active oxygen content in the bath. At the same time, the temperature in the bath is measured by the thermocouple.

The present invention may be embodied in other specific forms without departing from the spirit or essential attributes thereof and, accordingly, reference should be made to the appended claims, rather than to the foregoing specification, as indicating the scope of the invention.

I claim:

1. An oxygen sensor of the immersion type for measuring the active oxygen content in a bath of molten metal comprising a measuring head adapted to fit on the end of a carrier, said head having a portion which supports an electro-chemical cell, said cell including an oxygen ion conductive solid electrolyte projecting from said head, a solid reference material juxtaposed to one surface of said oxygen ion conductive solid electrolyte, means for reducing the thermal shock to which said oxygen ion conductive solid electrolyte is subjected after initial immersion including a shield, said shield cooperating with said head to envelop said oxygen ion conductive solid electrolyte, said shield having its inner periphery juxtaposed to and in thermal contact with the opposite surface of said oxygen ion conductive solid electrolyte, said shield being constructed of a metal which melts below 2800° F. whereby the shield will be consumable by a bath of molten steel for exposing said oxygen ion conductive solid electrolyte to the bath, and a second shield supported by said head for protecting said first mentioned shield and said cell during passage through slag.

2. A sensor in accordance with claim 1 wherein said oxygen ion conductor is stabilized zirconium oxide.

3. A sensor in accordance with claim 1 wherein said oxygen ion conductor is a tube having a closed end containing the reference material $CrCr_2O_3$.

4. A sensor in accordance with claim 1 wherein said first shield is a low carbon steel tube surrounding said oxygen ion conductor and having one end embedded in said head.

5. A sensor in accordance with claim 1 wherein said cell includes a metal ring circumscribing said conductor.

6. A sensor in accordance with claim 1 including a contact member connected to said head at the end thereof opposite from said cell, said contact member supporting first and second contact portions of electrical conductors coupled to said cell, a thermocouple projecting from said head alongside said cell, a third contact portion connected to one leg of said thermocouple and supported by said contact member, the other leg of said thermocouple being connected to said first contact portion.

7. A sensor in accordance with claim 6 wherein said contact portions are circumferentially spaced from each other and at different locations along said contact member.

8. An oxygen sensor having an oxygen ion conductive solid electrolyte as part of an electrochemical cell projecting from a head, a tubular metal shield enveloping said electrolyte and having one end imbedded in said head, the other end of said shield being closed, the inner periphery of said shield being juxtaposed to the outer periphery of said solid electrolyte with a fit providing thermal contact therebetween, said shield being a metal which melts below 2800° F. whereby the shield will be consumable by a bath of molten steel after immersion for exposing said solid electrolyte to the bath.

* * * * *